US008680086B2

(12) United States Patent
Hicks, Jr. et al.

(10) Patent No.: US 8,680,086 B2
(45) Date of Patent: Mar. 25, 2014

(54) METHODS FOR CHRONIC PAIN MANAGEMENT AND TREATMENT USING HCG

(75) Inventors: Edson Conrad Hicks, Jr., Phoenix, AZ (US); Constance T. Dutton, San Diego, CA (US)

(73) Assignee: Neuralight HD, LLC, Phoenix, AZ (US)

( * ) Notice: Subject to any disclaimer, the term of this patent is extended or adjusted under 35 U.S.C. 154(b) by 0 days.

(21) Appl. No.: 13/211,101

(22) Filed: Aug. 16, 2011

(65) Prior Publication Data

US 2012/0265712 A1 Oct. 18, 2012

Related U.S. Application Data

(60) Provisional application No. 61/475,908, filed on Apr. 15, 2011.

(51) Int. Cl.
*A61K 31/33* (2006.01)
*A01N 43/00* (2006.01)

(52) U.S. Cl.
USPC .............................. 514/183; 514/9.7; 705/500

(58) Field of Classification Search
None
See application file for complete search history.

(56) References Cited

U.S. PATENT DOCUMENTS

| | | | |
|---|---|---|---|
| 4,689,222 | A | 8/1987 | McMichael |
| 4,968,299 | A | 11/1990 | Ahlstrand et al. |
| 5,384,132 | A | 1/1995 | De Meere et al. |
| 5,677,275 | A | 10/1997 | Lunardi-Iskandar et al. |
| 5,929,028 | A | 7/1999 | Skrabanja et al. |
| 6,706,681 | B1 | 3/2004 | Samaritani et al. |
| 7,101,847 | B2 | 9/2006 | McMichael |
| 7,405,197 | B2 | 7/2008 | Menezo |
| 8,143,220 | B2 | 3/2012 | Weiss et al. |
| 2002/0058656 | A1 | 5/2002 | Ockert |
| 2002/0123670 | A1 | 9/2002 | Goetzke et al. |
| 2004/0072731 | A1 | 4/2004 | McMichael |
| 2006/0258568 | A1* | 11/2006 | Huber ................................ 514/8 |
| 2008/0039389 | A1 | 2/2008 | Weiss et al. |
| 2009/0081205 | A1 | 3/2009 | Weiss et al. |
| 2010/0004172 | A1 | 1/2010 | Khan et al. |
| 2012/0265129 | A1 | 10/2012 | Hicks, Jr. et al. |
| 2013/0196914 | A1 | 8/2013 | Hicks, Jr. et al. |

OTHER PUBLICATIONS

David, "Injection Method", 2007.*
Woolf, Pain Mar. 2011;152(3 Suppl):S2-15 Epub Oct. 18, 2010.*
Yang et al, J. Urol Sep. 2003;1170 (3).*
Paulson et al, Expert Rev. Obstet. Gynecol. 2(1), 37-50 (2007).*
Hashimoto, T., et al., "Chorionic Gonadotropin Preparation as an Analgesic", Archives of Internal Medicine, Feb. 1981. vol. 141, downloaded from www.archinternmed.com.
Kawasaki, Y., et al., "Cytokine Mechanisms of Central Sensitization: Distinct and Overlapping Role of Interleukin-1B, Interleukin-6, and Tumor Necrosis Factor-a in Regulating Synaptic and Neuronal Activity in the Superficial Spinal Cord", The Journal of Neuroscience, May 14, 2008, vol. 28, No. 20, pp. 5189-5194.
Huber, A., et al., "Effect of highly purified human chorionic gonadotropin preparations on the gene expression signature of stromal cells derived from endometriotic lesions: potential mechanisms for the therapeutic effect of human chorionic gonadotropin in vivo", Fertility and Sterility, Oct. 2, 2007, vol. 88, No. 2, pp. 1232-1239.
Stone, L.S., et al., "In Search of Analgesia: Emerging Roles of GPCRs in Pain", Molecular Interventions, Oct. 2009, vol. 9, No. 5, pp. 234-251.
Hu, L., et al., "Essential Role of G Protein-gated Inwardly Rectifying Potassium Channels in Gonadotropin-induced Regulation of GnRH Neuronal Firing and Pulsatile Neurosecretion", The Journal of Biological Chemistry, Sep. 1, 2006, vol. 281, No. 35, pp. 25231-25240.
Meng, X.L., et al., "Human Chorionic Gonadotropin Induces Neuronal Differentiation of PC12 Cells through Activation of Stably Expressed Lutropin/Choriogonadotropin Receptor", Endocrinology, 2007, vol. 148, No. 12, pp.
Tennant, F., "Human Chorionic Gonadotropin: Emerging Use in Pain Treatment", Prepared for Practical Pain Management.
Costigan, M., et al., "Neuropathic Pain: A Maladaptive Response of the Nervous System to Damage", Annual Review of Neurosciences, 2009, vol. 32, pp. 1-32.
Recla, J.M., "New and emerging therapeutic agents for the treatment of fibromyalgia: an update", Journal of Pain Research, Jul. 21, 2010, vol. 3, pp. 89-103.
Foulkes, T., et al., "Pain Genes", PLoS Genetics, Jul. 2008, vol. 4, No. 7, www.plosgenetics.org.
Apkarian, A.V., et al., "Pain and the brain: Specificity and plasticity of the brain in clinical chronic pain", Pain, 2011, vol. 152, pp. S49-S64.
Hicks, E.C., et al., "Daily Low Dose HCG: Neuroplasticity and Chronic Pain Control", Pain Article, Jun. 21, 2011.
Tennant, F., "Hormone Therapies: Newest Advance in Pain Care", Practical Pain Management, May 2011, pp. 98-105.
Abdallah et al., "Human fetal nongonadal tissues contain human chorionic gonadotropin/luteinizing hormone receptors," *J Clin Endocrinol Metab.*, 89(2):952-956, Feb. 2004.

(Continued)

*Primary Examiner* — Brandon Fetterolf
*Assistant Examiner* — Jean Cornet
(74) *Attorney, Agent, or Firm* — Fish & Richardson P.C.

(57) ABSTRACT

A gonadotropin is administered within a surprisingly effective narrow range for the purpose of treating chronic pain or other central sensitization sequelae. In one aspect, a recipient is provided with at least one of human chorionic gonadotropin (HCG), a pharmaceutically active HCG analogue, and a pharmaceutically active metabolite of the HCG or analogue at a dosage selected to provide, or be equivalent to, a human subcutaneous dosage of between 120 IU/day and 170 IU/day of HCG, and more preferably between 140 IU/day and 160 IU/day of HCG. A kit is also described, which includes a supply of the HCG-related drug, and a label that identifies chronic pain or central sensitization as an indication of the drug.

28 Claims, 3 Drawing Sheets

(56) References Cited

OTHER PUBLICATIONS

Al-Hader et al., "Novel expression of functional luteinizing hormone/chorionic gonadotropin receptors in cultured glial cells from neonatal rat brains," *Biol Reprod.*, 56(2):501-507, Feb. 1997.

Bair et al., "Association of depression and anxiety alone and in combination with chronic musculoskeletal pain in primary care patients," *Psychosom Med.*, 70(8):890-7. Epub Sep. 2008.

Bradley, "Pathophysiology of fibromyalgia," *Am J Med.*, 122(12 Suppl):S22-30, Dec. 2009.

Colucci-D'Amato et al., "The end of the central dogma of neurobiology: stem cells and neurogenesis in adult CNS," *Neurol Sci.*, 27(4):266-270, Sep. 2006.

Gallego et al., "The pregnancy hormones human chorionic gonadotropin and progesterone induce human embryonic stem cell proliferation and differentiation into neuroectodermal rosettes," *Stem Cell Res Ther.*, 1(4):28, Sep. 2010.

Greene and Tischler, "Establishment of a noradrenergic clonal line of rat adrenal pheochromocytoma cells which respond to nerve growth factor," *Proc Natl Acad Sci U S A.*, 73(7):2424-2428, Jul. 1976.

Kashyap et al., "Assisted reproductive technology and the incidence of ovarian cancer: a meta-analysis," *Obstet Gynecol.*, 103(4):785-794, Apr. 2004.

Keay et al., "The role of hCG in reproductive medicine," *BJOG.*, 111(11):1218-1228, Nov. 2004.

Kristiansen et al., "Introduction and Validation of DoloTest®: a new health-related quality of life tool used in pain patients," *Pain Pract.*, 10(5):396-403, Sep.-Oct. 2010.

Latremoliere and Woolf, "Central sensitization: a generator of pain hypersensitivity by central neural plasticity," *J Pain.*, 10(9):895-926, Sep. 2009.

Lei and Rao, "Neural actions of luteinizing hormone and human chorionic gonadotropin," *Semin Reprod Med.*, 19(1):103-109, 2001.

Lei et al., "Novel expression of human chorionic gonadotropin/luteinizing hormone receptor gene in brain," *Endocrinology.*, 132(5):2262-2270, May 1993.

Maletic and Raison, "Neurobiology of depression, fibromyalgia and neuropathic pain," *Front Biosci (Landmark Ed)*. 14:5291-5338, Jun. 2009.

Maymó et al., "Up-regulation of placental leptin by human chorionic gonadotropin," *Endocrinology*, 150(1):304-313, Epub Sep. 2008.

Narayan et al., "A biologically active single chain human chorionic gonadotropin analog with altered receptor binding properties," *Endocrinology*, 141(1):67-71, Jan. 2000.

Nijs et al., "Treatment of central sensitization in patients with 'unexplained' chronic pain: what options do we have?" *Expert Opin Pharmacother.*, 12(7):1087-1098, Epub Jan. 2011.

Patil and Nagaraj, "The effect of human chorionic gonadotropin (HCG) on functional recovery of spinal cord sectioned rats," *Acta Neurochir (Wien).*, 69(3-4):205-218, 1983.

Post, "Kindling and sensitization as models for affective episode recurrence, cyclicity, and tolerance phenomena," *Neurosci Biobehav Rev.*, 31(6):858-873, Epub Apr. 2007.

Rao and Lei, "The past, present and future of nongonadal LH/hCG actions in reproductive biology and medicine," *Mol Cell Endocrinol.*, 269(1-2):2-8, Epub Feb. 2007.

Remington, The Science and Practice of Pharmacy, 21st Edition, p. 2033, 2005.

Simeons, *Pounds and Inches*, p. 24, retrieved from the Internet: URL:<http://www.hcgbodyshaper.com/simeon.pdf>, 1953.

Stella et al., *Prodrugs: Challenges and Rewards. Part 1*, p. 24, New York: Published by AAPS Press and Springer; 2007.

Tennant, "Human Chorionic Gonadotropin in Pain Treatment," *Practical Pain Management*, vol. 9, issue 5, 5 pages, Jun. 2009.

Yunis, "Fibromyalgia and overlapping disorders: the unifying concept of central sensitivity syndromes," *Semin Arthritis Rheum.*, 36(6):339-356, Epub Mar. 2007.

Zreik et al., "Fertility drugs and the risk of breast cancer: a meta-analysis and review," *Breast Cancer Res Treat*, 124(1):13-26, print Nov. 2010, Epub Aug. 2010.

International Search Report in PCT/US2012/33828 mailed Sep. 21, 2012, 4 pages.

International Preliminary Report on Patentability and Written Opinion for PCT/US2012/033828, issued Oct. 15, 2013, 6 pages.

US 7,488,594, 02/2009, Saxena et al. (withdrawn)

\* cited by examiner

METHODS FOR CHRONIC PAIN MANAGEMENT AND TREATMENT USING HCG

This application claims the benefit of priority to U.S. Provisional Application Ser. No. 61/475908, filed Apr. 15, 2011 and is incorporated herein by reference in its entirety.

FIELD OF THE INVENTION

The field of the invention is chronic pain management, and more specifically to administration of specific low doses of human chorionic gonadotropin (HCG).

BACKGROUND

An ongoing and pervasive problem in the medical community is treating patients with chronic pain syndromes. It is well recognized today that chronic pain is fundamentally different from acute pain, also referred to as nociceptive pain, which is pain resulting from a mechanical, chemical, metabolic or inflammatory insult.

It has been recognized by some that since the mechanisms and pathways for chronic and acute pain are physiologically different, they require different approaches for treatment. Unfortunately, many in the medical community continue to treat patients suffering from chronic pain syndromes with agents designed to address acute nociceptive pain pathways. Such methods are often fraught with toxicity and dependence issues, and in the end are generally unsatisfactory in ending pain and/or improving quality of life. A new diagnostic paradigm and treatment protocol is therefore needed to address chronic pain.

Central sensitization is a newly recognized diagnostic entity that underlies a broad range of phenotypic syndromes, including various chronic pain and mood disorders. As used herein, central sensitization means an abnormal state of functioning of the neurons and circuitry of the central pain intensity, perception and modulation systems; due to synaptic, chemical, functional and/or structural changes, in which pain is no longer coupled, as acute nociceptive pain is, to particular peripheral stimuli. Instead the central nervous system (CNS) initiates, maintains and contributes to the generation of pain hypersesensitivity and perception, absent a peripheral stimulus.

The present inventors consider the following to be a non-exhaustive listing of conditions associated with (causative or resulting from) central sensitization, each of which is thought to be applicable to humans or other vertebrates.

1. Autonomic neuropathies
2. Chronic joint pain associated metabolic neuropathy
3. Chronic joint pain associated with inflammation
4. Fibromyalgia
5. Irritable bowel syndrome
6. Migraine
7. Post Herpetic neuralgia
8. Post surgical pain syndromes
9. Rheumatoid, arthritic, psoriatic and other chronic arthropathies
10. Spinal nerve compression syndromes associated with neoplasia and/or disc herniation
11. Trigeminal neuralgia Central sensitization is currently thought to be established via a well characterized constellation of cellular changes termed, neuroplasticity. Neuroplasticity consists of the physical remodeling of neuronal and microglial cytoarchitecture; such as changes in synaptic gap junctions, membrane excitability shifts due to ion channel modulation, and gene transcription. Neuroplasticity changes can be bi-directional. In other words, appropriately functioning cells can undergo remodelling that results in a dysfunctional operating state creating what the current inventors appreciate as disease (pain or mood disorders for example). Conversely, these neuroplasticity mediated dysfunctional changes can be reversed with a return to 'normal' functioning, which can correspond clinically to a resolution of a 'disease' state.

Central sensitization involves, in part, shifts in gene transcription involved in nociception and pain modulation. Huber, et al has clearly shown this phenomenon occurring at specific HCG concentration levels in endometriotic tissue. Some of the specific genes identified in this study were genes encoding for G-protein coupled receptor (GPCR) function. See:

1. Huber A, Hudelist G, Knofler N, Saleh L, Huber J C, Singer C F. Effect of highly purified human chorionic gonadotropin preparations on the gene expression signature of stromal cells derived from endometriotic lesions: potential mechanisms for the therapeutic effect of human chorionic gonadotropin in vivo. October 2007 Fertility and Sterility Vol. 88, No. Suppl 2.
2. Foukes T, Wood J N. Pain Genes. PLoS Genetics. July 2008 (4)7:e1000086.

Pain, in general, represents a hyper-excitatory state of neuronal tissue associated with an increase in action potential firing. Action potential generation is the result of increased amplitude and/or frequency of electrical signaling. This is created by the cellular integration of changes in molecular signaling, ion gradients and gene expression resulting in the perception of acute or chronic discomfort.

Pain transmission and modulation through the central nervous system network of neurons and support glial cells (microglia and astrocytes) is largely under the control of a large family of cellular receptors known as G protein-coupled receptors (GPCRs). The function of these complex transmembrane receptors is to transduce extracellular stimuli into intracellular signaling including gene transcription. GPCRs modulate and/or mediate virtually all physiologic processes in eukaryotic organisms, including acute and chronic pain. An estimated 90% of all known GPCRs are expressed in the central nervous system. 80% of the currently proposed GPCR families have a known role in modulation of pain. Similarly, most of the identified genes associated with pain modulation are GPCR related genes. (1)

The LH/HCG receptor is a GPCR.

Stone L S, Molliver D C. In search of analgesia: Emerging role of GPCRs in pain. Molecular Interventions. 2009 (9):5; 234-251.

The LH/HCG receptor complex specifically has been specifically shown to complex with the Gαi/o group resulting in modulation of neurotransmission. (2) Gαi/o proteins mediate the widespread inhibitory effects of many neurotransmitters and they mediate the effects of almost all analgesic GCPR agonists (1).

Stone L S, Molliver D C. In search of analgesia: Emerging role of GPCRs in pain. Molecular Interventions. 2009 (9):5; 234-251.

Hu L, Wada k, Mores N, Krsmanovic L Z, Catt K J. Essential role of G protein-gated inwardly rectifying potassium channels in gonadotropin-induced regulation of GnRH neuronal firing and pulsatile neurosecretion. Jour Biol Chem. 2006:281(35); 25231-25240.

Due to the multiplicity of pathways involved in establishing central sensitization, chronic pain is a complex phenomenon that can be difficult to treat with single-pathway-activeagent therapy. See Latremoliere A, Woolf C J. *Central sensitization: A generator of pain hypersensitivity by central neural plasticity*. J Pain. 2009 September; 10(9):895-926. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

This may explain why there remains a critical dearth of effective medical interventions to treat chronic pain disorders. Traditional pharmaceutical approaches generally deal with a single involved pathway, which tends to yield less than ideal results and is often associated with significant toxicity. For example, the treatment options most commonly investigated to date consist of centrally acting drugs. These include ketamine, dextromethorphan, gabapentin, pregabalin, duloxetine, milnacipran, lamotrigene; and not all of these have reached human trials at this time. Each has demonstrated a poor therapeutic index in trials.

Thus, there is still a need for apparatus, systems, and methods for treating chronic pain, and more generally central sensitization that approaches this disorder in a pleiotropic fashion.

SUMMARY OF THE INVENTION

The inventive subject matter provides apparatus, systems, and methods in which a gonadotropin is administered within a surprisingly effective narrow range for the purpose of treating chronic pain or other central sensitization sequelae.

In one aspect, contemplated methods involve communicating with a person, non-human animal, subject or other recipient to determine whether that recipient suffers from chronic pain, and then facilitating the recipient's taking of at least one of human chorionic gonadotropin (HCG), a pharmaceutically active HCG analogue, and a pharmaceutically active metabolite of the HCG or analogue. Preferably the dosage is selected to provide, or be equivalent to, a human subcutaneous dosage of between 120 IU/day and 170 IU/day of HCG. More preferably, the dosage is selected to provide, or be equivalent to, a human subcutaneous dosage of between 140 IU/day and 160 IU/day of HCG.

Contemplated manners of communication include procuring a written and/or oral symptom history, and especially focusing on whether the recipient has one or more of fibromyalgia, irritable bowel syndrome, chronic arthropathy, inflammatory pain, post herpetic neuralgia, trigeminal neuralgia, and migraine. Such communication can be performed synchronously between a health care professional and the recipient, as for example in a doctor's office or over the phone, and/or asynchronously, as for example using physical mail, electronic mail, and so forth. It is also contemplated to conduct a physical test that aids in distinguishing between nociceptive pain and central sensitization that the recipient may have.

Contemplated manners of facilitating the recipient's taking of the drug(s) include administering the drug(s), issuing a prescription for the drug(s), suggesting use of the drug(s), as in a book or article, and/or providing the recipient (directly or indirectly) with contact information for a supply of the drug(s). It is contemplated that one or more of the drugs could be self-administered by the recipient.

The drug(s) are preferably taken as a monotherapy for the central sensitization, but could be combined with other drugs and/or non-drug treatments, including for example, lifestyle changes. It is preferred that the drug(s) is/are taken in the absence of concurrent opioid pain treatment, and in the absence of concurrent treatment with another gonadotropic substance.

In some instances a clinician or other provider may have been administering or recommending HCG for some other purpose, or in some other dosage, not realizing that HCG can be effective to ameliorate chronic pain or central sensitization as claimed herein. In such instances it is contemplated that the provider receive information that HCG may have a peak effect on central sensitization between 120 IU/day and 170 IU/day, inclusive, and can thereafter administer or recommend HCG, a pharmaceutically active HCG analogue, or a pharmaceutically active metabolite of the HCG or analogue as claimed herein.

It is contemplated that a kit could include (a) a supply of a drug selected from the group consisting of at least one of HCG, a pharmaceutically active HCG analogue, and a pharmaceutically active metabolite of the HCG or analogue, and (b) a label that identifies at least one of chronic and pain central sensitization as an indication for the drug.

In some aspects of preferred embodiments, the label identifies a daily dosage regimen at or equivalent to a subcutaneous dosage of human chorionic gonadotropin (HCG) between 120 IU/day and 170 IU/day, inclusive, with respect to chronic pain relief. In other aspects of some preferred embodiments, the label identifies a daily dosage regimen at or equivalent to a subcutaneous dosage of human chorionic gonadotropin (HCG) between 140 IU/day and 160 IU/day, inclusive, with respect to chronic pain relief.

In yet other aspects of preferred embodiments, a kit can include a vial having a lyophilized preparation of the drug that is suitable for injection when mixed with a diluent. The drug could be disposed in an auto-inject or a dial up dosing pen. Alternatively or additionally, a kit could include a container that includes the drug in an orally available composition.

A provider need not actively communicate with the recipient, but could determine in some other manner that the recipient might suffer from a central sensitization disorder. For example, the step of determining could comprise initiating a plurality of laboratory tests that includes: (a) at least one test selected from a first group consisting of dynamic tactile allodynia, secondary punctate/pressure hyperalgesia, temporal summation, and sensory after effects, and (b) at least one other test selected from a second group consisting of SMAC 25, fMRI, Neuro-Endocrine profile (neurotransmitters and hormones), CSF study (substance P, glutamate, NGF, BDNF), cytokines profile, genetic polymorphism profile, food allergy panel, and heavy metals analysis panel.

In other aspects, the step of determining comprises (i) determining that the subject may suffer from central sensitization due to a trauma, and (ii) providing the subject with access to the drug peritraumatically. In yet other aspects of some preferred embodiments, the trauma is a surgery, and the drug is administered perioperatively.

Various objects, features, aspects, and advantages of the inventive subject matter will become more apparent from the following detailed description of preferred embodiments, along with the accompanying drawing figures in which like numerals represent like components.

DETAILED DESCRIPTION

Figure 1:
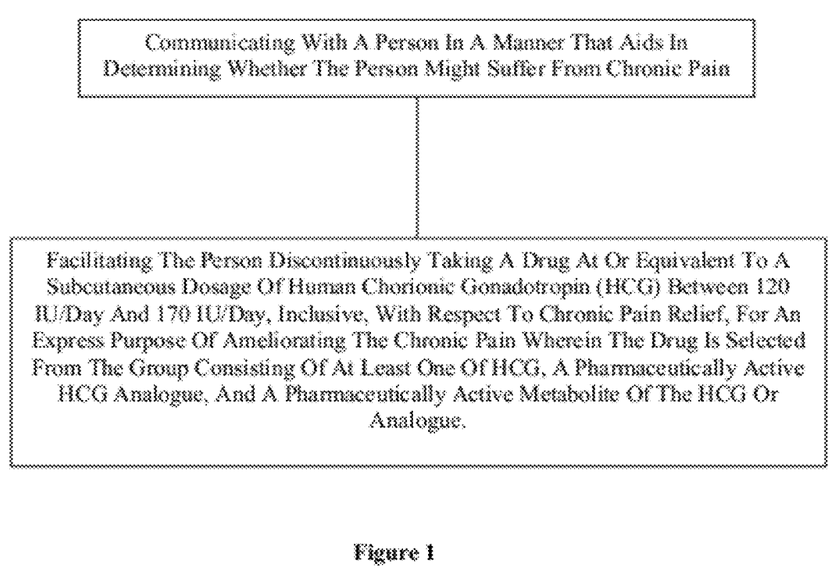
FIG. 1 is a schematic of one preferred embodiment of a method of interacting with a person.

In FIG. 1 a schematic of a method of interacting with a person is shown. The method includes the steps of: (i) communicating with the person in a manner that aids in determining whether the person might suffer from chronic pain; and (ii) facilitating the person discontinuously taking a drug at or equivalent to a subcutaneous dosage of human chorionic gonadotropin (HCG) between 120 IU/day and 170 IU/day, inclusive, with respect to chronic pain relief, for an express purpose of ameliorating the chronic pain, wherein the drug is selected from the group consisting of at least one of HCG, a pharmaceutically active HCG analogue, and a pharmaceutically active metabolite of the HCG or analogue.

As used herein, the term pharmaceutically active HCG analogue means a compound that, with respect to amelioration of chronic pain or other sequelae of central sensitization, has either (i) has at least a partial biological activity of HCG (e.g., mutant, truncated form, chemically modified), or (ii) can bind to HCG receptors, either an agonist or neutral ligand. As used herein the term "analogues" includes prodrugs of HCG.

As used herein, a "prodrug" means a modification of a contemplated compound, wherein the modified compound exhibits less pharmacological activity (as compared to the modified compound) and wherein the modified compound is converted within a target cell (e.g., B-cell) or target organ/anatomic structure (e.g., joint) back into the modified form. For example, conversion of contemplated compounds into prodrugs may be useful where the active drug is too toxic for safe systemic administration, or where the contemplated compound is poorly absorbed by the digestive tract or other compartment or cell, or where the body breaks down the contemplated compound before reaching its target. Thus, it should be recognized that the compounds according to the inventive subject matter can be modified in numerous manners, and especially preferred modifications include those that improve one or more pharmacokinetic and/or pharmacodynamic parameter. For example, one or more substituents may be added or replaced to achieve a higher area under the curve (AUC) of HCV in serum.

As used herein, the term pharmaceutically active metabolite means any compound resulting from in vivo metabolism of HCG or an HCG analogue (for example, via proteolytic digest, glycoslyation, phosphorylation, sulfuration, etc), where the metabolite is effective with respect to amelioration of chronic pain or other sequelae of central sensitization.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

The step of communicating can comprise procuring from the person at least one of a written and an oral symptom history. The symptom history can be used to assist in determining whether the person has at least one of fibromyalgia, irritable bowel syndrome, chronic arthropathy, inflammatory pain, post herpetic neuralgia, trigeminal neuralgia, and migraine.

The step of communicating can be performed either synchronously between a health care professional and the person, or alternatively, asynchronously between a health care professional and the person using physical mail or electronic communication.

The step of facilitating can comprise issuing a prescription for use of the drug by the person. In addition, the step of facilitating can comprise providing the person with contact information from which the person can procure a supply of the drug.

The dosage is preferably at or equivalent to a subcutaneous dosage of between 140 IU/day and 160 IU/day, inclusive, with respect to chronic pain relief.

The method of FIG. 1 can further include the step of conducting a physical test that aids in distinguishing between nociceptive pain and central sensitization that the person may have.

The method can also include the step of assisting in procuring the drug for the person as a monotherapy for the central sensitization. In addition, the method can include the step of assisting in procuring a composition for the person in adjunct to the drug that facilitates coupling to the Gα, i/o, G-Protein Coupled Receptor (GPCR) subunits, facilitating and/or enhancing an analgesic effect.

It is also contemplated that one can perform the step of "facilitating" after receiving information that HCG may have a peak effect on central sensitization between 120 IU/day and 170 IU/day, inclusive.

Equivalents of a subcutaneous dosage of HCG can include all suitable modes of administration, such as intramuscularly, subdermally, orally dissolving tab, sublingually as a liquid, transdermally, rectally, and via subdermal slow release pellets.

The method shown in FIG. 1 can be used to treat numerous disorders related to chronic pain and central sensitization. For example: fibromyalgia, rheumatoid arthritis, osteoarthritis, chronic arthropathy, spinal nerve compression syndromes associated with neoplasia and/or disc herniation, chronic joint pain of any etiology associated with inflammation and/or structural joint abnormalities, post herpetic neuralgia, trigeminal neuralgia, chronic metabolic neuropathy associated with chronic pain, migraine, inflammatory pain, post surgical pain syndromes, irritable bowel syndrome, autonomic neuropathies, and chronic pain syndrome associated with activation of central sensitization pathways.

It is also contemplated that the "person" can include humans, pets, and mammals.

Figure 2:
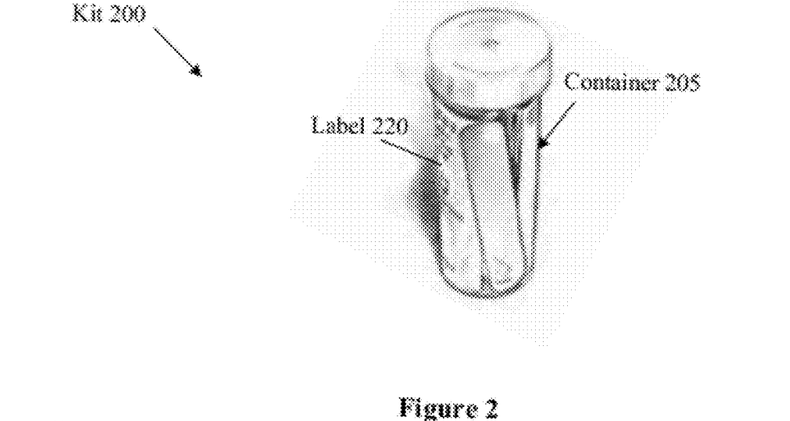
FIG. 2 is a perspective view of one preferred embodiment of a kit that includes a supply of a drug and a label.

FIG. 2 one preferred embodiment of a kit 200. Kit 200 includes a container 205. Container 205 holds a drug 210 and has an exterior label 220.

Drug 210 is preferably selected from the group consisting of at least one of HCG, a pharmaceutically active HCG analogue, and a pharmaceutically active metabolite of the HCG or analogue. Drug 210 is an orally administered capsule. It is also contemplated that drug 210 could comprise other dosage forms.

It should be recognized that all formulations are deemed suitable for use herein and especially include oral and parenteral formulations. For example, for oral administration, contemplated compositions may be in the form of a tablet, orally dissolving tablet, capsule, suspension, or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier. In especially preferred aspects, it is contemplated that the formulation is suitable for topical administration, administration via aerosol, and for intrathecal administration. Consequently, especially suitable formulations may be sterile aqueous solutions for topical spray or drop administration, or application as a tincture. Alternatively, suitable topical formulations include creams, ointments, foams, lotions, emulsions, etc. Furthermore, where the compound is formulated for intrathecal administration (e.g., in the treatment of spinal cord injury), it is preferred that the compound is prepared as an injectable solution, suspension, or emulsion. In still further contemplated formulations, contemplated compounds may be formulated for aerosol delivery (e.g., micropowderized, coated onto a dispersible carrier, dissolved in atomizable solvent, etc.)

It should be appreciated that the choice of the particular formulation and carrier will at least in part depend on the specific use and type of compound. There are numerous manners of drug formulation known in the art, and all of those are deemed suitable for use herein (see e.g., Pharmaceutical Preformulation and Formulation: A Practical Guide from Candidate Drug Selection to Commercial Dosage Form by Mark Gibson; Informa HealthCare, ISBN: 1574911201; or Advanced Drug Formulation Design to Optimize Therapeutic Outcomes by Robert O. Williams, David R. Taft, and Jason T. McConville; Informa HealthCare; ISBN: 1420043870).

Although age, gender and weight of a recipient of HCG treatment for chronic pain does not appear with current studies to affect the preferred therapeutic ranges, it is contemplated that the amount of therapeutically active compound that is administered and the dosage regimen for treating a disease condition with the compounds and/or compositions of this invention could depend on one of more of a variety of factors, including the age, weight, sex and medical condition of the subject, the severity of the disease, the route and frequency of administration, and the particular compound employed, and thus may vary widely.

Label 220 identifies at least one of chronic pain and central sensitization as an indication for the drug. Label 220 also identifies a daily dosage regimen at or equivalent to a subcutaneous dosage of human chorionic gonadotropin (HCG) between 120 IU/day and 170 IU/day, inclusive, with respect to chronic pain relief. Alternatively, label 220 could identify a daily dosage regimen at or equivalent to a subcutaneous dosage of human chorionic gonadotropin (HCG) between 140 IU/day and 160 IU/day, inclusive, with respect to chronic pain relief.

Kit 200 could also include a vial that contains a lyophilized preparation of the drug that is suitable for injection when mixed with a diluent.

Figure 3:
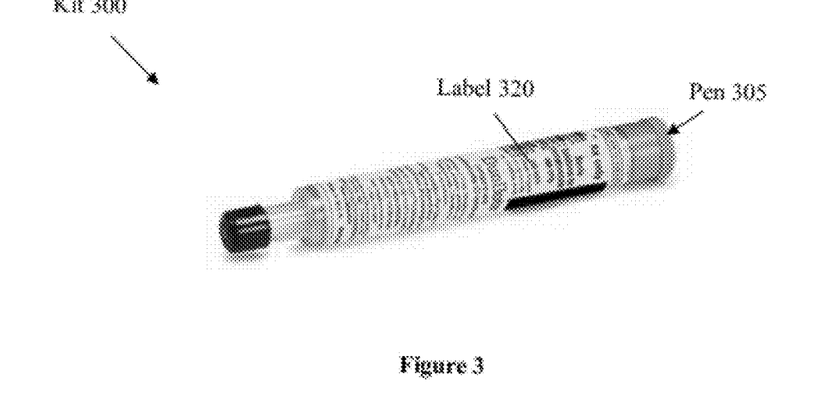
FIG. 3 is a perspective view of an auto-inject dosing pen.

FIG. 3 shows a kit 300, which includes an auto-inject dosing pen 305. Pen 305 has a drug 310 and an exterior label 320. Drug 310 is similar to drug 210 except that drug 310 is in a liquid form. Label 320 is similar to label 210, except that it contains information relevant to injection rather than oral administration.

Figure 4:
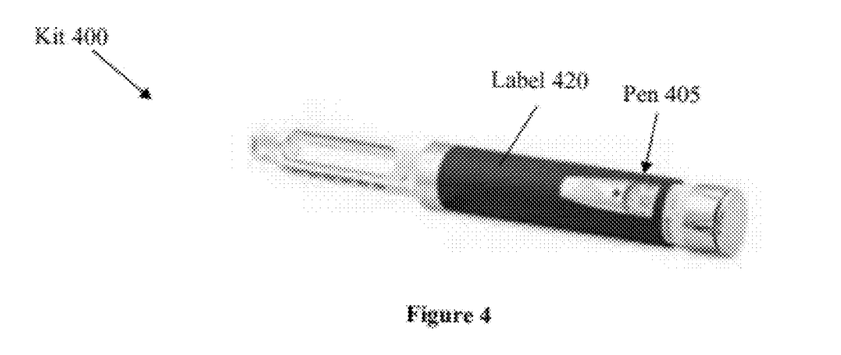
FIG. 4 is a perspective view of a dial-up dosing pen.

FIG. 4 shows a kit 400, which includes an dial-up dosing pen 405. Pen 405 has a drug 410 and an exterior label 420. Drug 410 is similar to drug 310. Label 420 is similar to label 210, except that it contains information relevant to injection rather than oral administration.

Figure 5:
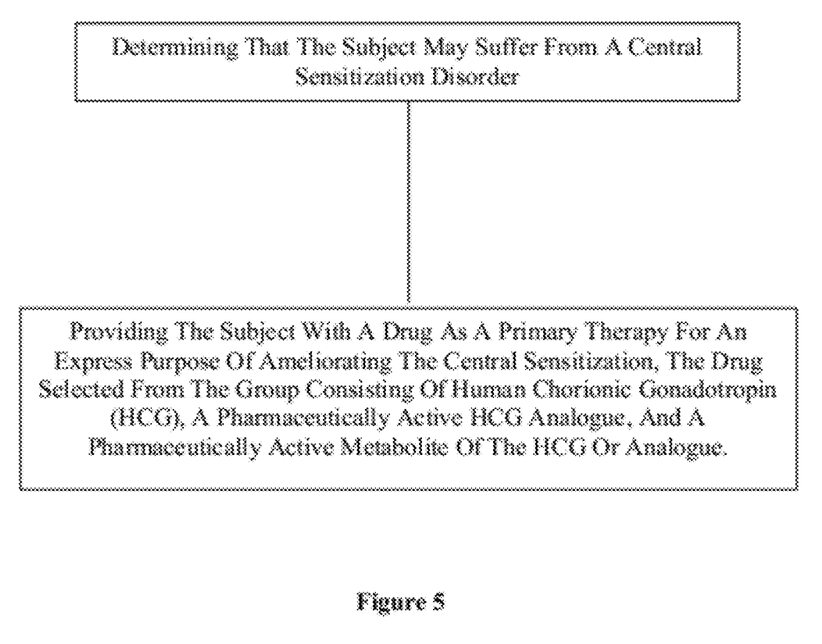
FIG. 5 is a schematic of one preferred embodiment of a method of treating a subject.

In FIG. 5, a schematic of a method of treating a subject is shown. The method includes the steps of: (i) determining that the subject may suffer from a central sensitization disorder; and (ii) providing the subject with a drug as a primary therapy for an express purpose of ameliorating the central sensitization. The drug is either human chorionic gonadotropin (HCG), a pharmaceutically active HCG analogue, or a pharmaceutically active metabolite of the HCG or analogue.

The step of determining that the subject may suffer from central sensitization disorder can include initiating a plurality of laboratory tests. Such laboratory tests may include: (i) at least one test selected from a first group consisting of dynamic tactile allodynia, secondary punctate/pressure hyperalgesia, temporal summation, and sensory after effects, and (b) at least one other test selected from a second group consisting of SMAC 25, fMRI, Neuro-Endocrine profile (neurotransmitters and hormones), CSF study (substance P, glutamate, NGF, BDNF), cytokines profile, genetic polymorphism profile, food allergy panel, and heavy metals analysis panel.

In addition, the step of determining that the subject may suffer from central sensitization disorder can include: (i) determining that the subject may suffer from central sensitization due to a trauma, and (ii) providing the subject with access to the drug peritraumatically. The trauma can include a surgery, traumatic brain injuries (TBI), stroke, transient ischemic attack (TIA), motor vehicle accident, gunshot would, industrial accidents, assault, blunt trauma, repetitive traumatic sports injuries, eventful psychoemotional trauma (rape, war, natural catastrophies, but not limited to this list).

It is especially contemplated that peritraumatic administration can include perioperative administration. For example, for surgical procedures known to be associated with significant long term pain syndromes (i.e., thoracotomy, mastectomy and amputations) post-operatively; where the drug is administered peri-operatively in an effort to prevent the development of central sensitization mediated post-op chronic pain syndromes; or alternatively, the drug can be administered to those with established central sensitization mediated post-operative pain for analgesia.

The step of providing the subject with a drug can include suggesting and/or instructing the subject to self-administer an amount of the drug at or equivalent to a subcutaneous dosage of human chorionic gonadotropin (HCG) between 120 IU/day and 170 IU/day, inclusive, with respect to chronic pain relief.

The method in FIG. 5 preferably does not include concomitantly treating the subject with an opioid pain treatment or another gonadotropic substance.

Case Study

Materials/Methods

Based on previous experience with pain control and established safety with human use of HCG (see The role of hCG in reproductive medicine. BJOG: an International Journal of Obstetrics and Gynaecology. November 2004, Vol. 111, pp. 1218-1228), the current inventors aimed at determining the efficacy of clinical use in a standardized fashion in a representative series of 24 patients (patient characteristics are presented in Table 1).

TABLE 1

Demographics, Diagnosis, and Treatment Group According to Each Patient of Study

| Patient # | Age (years) | Gender | Diagnosis | Treatment Group |
|---|---|---|---|---|
| 1 | 46 | Female | Disc pain | HCG Weight Loss |
| 2 | 56 | Female | Fibromyalgia | HCG Weight Loss |
| 3 | 56 | Female | Disc pain | HCG Weight Loss |
| 4 | 41 | Female | Headache | HCG Weight Loss |
| 5 | 45 | Female | Back pain | HCG Weight Loss |
| 6 | 41 | Female | Disc pain | HCG Weight Loss |
| 7 | 52 | Female | Fibromyalgia | HCG Weight Loss |
| 8 | 53 | Female | Osteoarthritis | HCG Weight Loss |
| 9 | 60 | Female | Osteoarthritis | HCG Weight Loss |
| 10 | 66 | Female | Fibromyalgia | HCG Weight Loss |

TABLE 1-continued

Demographics, Diagnosis, and Treatment Group According to Each Patient of Study

| Patient # | Age (years) | Gender | Diagnosis | Treatment Group |
|---|---|---|---|---|
| 11 | 61 | Female | Neuralgia | HCG Weight Loss |
| 12 | 78 | Female | Osteoarthritis | HCG Weight Loss |
| 13 | 61 | Female | Fibromyalgia/ Rheumatoid Arthritis | HCG Weight Loss |
| 14 | 30 | Male | Osteoarthritis | HCG Weight Loss |
| 15 | 53 | Male | Disc pain | HCG Pain |
| 16 | 53 | Female | Osteoarthritis | HCG Pain |
| 17 | 59 | Male | Osteoarthritis | HCG Pain |
| 18 | 42 | Female | Osteoarthritis | HCG Pain |
| 19 | 47 | Female | Rheumatoid Arthritis | HCG Pain |
| 20 | 47 | Female | Disc pain | HCG Pain |
| 21 | 44 | Female | Fibromyalgia | HCG Pain |
| 22 | 19 | Female | Osteoarthritis | HCG Pain |
| 23 | 43 | Male | Osteoarthritis | HCG Pain |
| 24 | 76 | Female | Osteoarthritis | HCG Pain |

The majority of patients listed were enrolled in an HCG weight loss program that required a 500 cal/day diet along with daily injections of 150 IU/day of HCG subcutaneously. HCG was provided to patients in a lyophilized powdered form for 5,000 IU or 10,000 IU vials for reconstitution prior to use and requiring refrigeration after mixing to maintain potency (HCG 5000 IU vials, KRS Global, Boca Raton, Fla.; HCG 10,000 IU vials, brand name Abraxis™; HCG 10,000 IU vials, brand name Pregnyl™). All HCG was sourced from major suppliers in China coming to the US from FDA approved and CGM P (Current Good Manufacturing Practices) compliant facilities. HCG from these facilities is either sourced from the urine of pregnant women (u-HCG) or from recombinant DNA (r-HCG) production protocols.

In our study, patients #13 and #20 had initial pain responses to r-HCG and continued identical sustained responses with substitution of u-HCG. Patient #2 initially had a pain response to u-HCG and subsequently used r-HCG and returned to u-HCG without a deviation in response.

Patients were allowed to continue medications during the diet, and were all placed on a specific nutritional support regimen which included a daily blend of multi-vitamins, digestive enzymes, probiotics, amino acids, potassium, magnesium, calcium, and 1-carnitine.

All cases except two required re-institution of daily subcutaneous injections of 150 IU HCG for pain control after a relapse of the pain subsequent to completion of the weight loss program. Patients returned to the office several weeks after completion of the weight loss program to report a return of pain and a desire to restart treatment. Universally, reinstitution of HCG treatment resulted in an identical clinical response that persisted in all patients as long as treatment was) continued. None of the patients, to date, developed tachyphylaxis or need for additional pain control.

There were two exceptions regarding the need for continued treatment: Patient #11, suffered from a shoulder girdle post herpetic neuralgia syndrome, requiring daily Oxycontin administration. She reported complete remission of her pain during her weight loss cycle and this response did not require continued HCG administration. At the time of this writing, the follow-up time has been over 12 months. Patient 13 suffered from RA requiring weekly Enbrel™ injections and she has not required treatment for over a year at this writing since her initial HCG exposure for RA associated pain.

Patients were carefully monitored for any treatment toxicity including transient hair loss, signs or symptoms of ovarian hyper-stimulation syndrome (OHS). However, accumulated clinical experience (e.g., The role of hCG in reproductive medicine. BJOG: an International Journal of Obstetrics and Gynaecology. November 2004, Vol. 111, pp. 1218-1228) indicate that such expected toxicities are usually associated with higher dosage HCG of above 1500 IU/day. The current inventors have observed no evidence of toxicity in any patients on continued treatment to date.

Patient responses were quantified utilizing the DoloTest™, a validated health-related quality of life (HRQoL) tool for pain patients that evaluates not only pain but also other areas of quality of life that chronic pain often severely impacts. [Ref: 4 Kristiansen K, Lyhgholm-Kjaerby P, Moe C. Introduction and Validation of DoloTest: A Health Related Quality of Life Tool Used in Pain Patients. Pain Practice 2010 September-October; 10(5):396-403]]

Patients responded to questions posed by the investigators regarding functioning level both before HCG exposure and after institution of HCG treatment. As responses were not graded in any way over time, there were only two end points to be evaluated: on and off HCG treatment.

In all instances there has been a significant or complete elimination of need for any additional pain control interventions. The need for continued visits to physicians' offices for therapy was eliminated. Most importantly, DoloTest™ indicators were all substantially improved for all patients listed. All patients answered all questions.

Results

SPSS v15.0 was used for all descriptive and inferential analyses. (See Table 2)

A total of 10 analyses were performed with multiple analyses being performed on the same data. To adjust for the increased chance of a Type I error, a Bonferroni correction was done to adjust the significance level for rejection of the Null hypothesis. Using this method, rejection of the Null hypothesis was determined for all analyses when the p-value was less than or equal to 0.005.(See Table 2)

A series of eight 2×2 mixed-ANOVA analyses were performed on the data. The between groups variable for all analyses was the patient group with two categories as mentioned above, and the within group independent variable was time; with two categories of (a) pre-treatment DoloTest score, and (b) post-treatment DoloTest score.

For each of the eight DoloTest™ domains analyzed for all patients in both groups, scores were significantly lowered or improved post-HCG treatment, with p-values<0.0005 for each domain analyzed.(See Table 2)

Pain and Mood:

Finally, two constructs were derived from the DoloTest™ instrument: (a) Physical Aspect and (b) Spiritual, Social and Sleep. Physical aspect included: Problems With Light Physical Activities, Problems with Strenuous Physical Activities, Problems Doing Your Job, and Reduced Energy and Strength. Social, Spiritual and Sleep aspect included: Low Spirit, Reduced Social Life and Problems Sleeping.

For each group, the summed score for each category was divided by the number of variables to obtain an average score for both pre and post treatment with HCG. A Pearson's correlation was then performed on the mean difference scores of the two constructs or groups to assess a linking of these two aspects of chronic pain fallout. Results were statistically significant (p<0.0005) suggesting a strong direct correlation, as we would expect, between the two constructs or groups, i.e., when scores increase or decrease for the physical aspect, scores move in a parallel fashion for the Spiritual/Social/

Sleep construct. Clearly, a direct correlation between the pain index and other DoloTest™ items score was seen both in the pre-treatment and the post-treatment groups. As noted above, and of particular interest, is the fact that for most of these patients (91.66%), the need for continued adjuvant treatment for pain, in addition to continued HCG administration, was eliminated.

For all patients listed, the time required to see a positive clinical response was immediate and within a 1-2 day window. For most patients treated, there was a need for continued HCG administration for maintenance of a continued response. In these patients, discontinuing HCG has consistently resulted in a return of their pain syndrome, at what was perceived to be the pre-treatment level. Re-instituting HCG therapy at 150 IU/day subcutaneously resulted promptly in pain relief within 1-2 days.

To date, no patient requiring continuous HCG administration for pain control has reported any decrease in response or need for additional pain treatment. The longest term patient in this series with such consistent response is Patient #9, now at 24 months.

Patients #11 and #13 both manifested a pain relief response in the context of their initial HCG weight loss cycle which continued to be fully sustained without the need for continued HCG administration or further clinical pain interventions. Patient #11 had a severe post herpetic neuralgia requiring multiple daily doses of narcotics that resolved completely with a single six week exposure to HCG and Patient #13 suffered from RA requiring weekly Enbrel injections and subsequently she has not required treatment for over a year since her initial HCG exposure.

For the remainder of patients, daily dosing of HCG at 140-170 IU/day has been required for continued pain control.

TABLE 2

MEASURES OF CENTRAL TENDENCY FOR PRE-TREATMENT AND POST-TREATMENT DOLOTEST ITEM SCORES FOR THE SAMPLE OVERALL (N = 24)

| DoloTest Item | M | SD | Mdn | Sample Range |
|---|---|---|---|---|
| Pain | | | | |
| Pre-Treatment | 65.83 | 18.91 | 64.50 | 27-97 |
| Post-Treatment | 15.00 | 12.32 | 11.50 | 0-50 |
| Problems with light physical activities | | | | |
| Pre-Treatment | 60.17 | 24.65 | 65.00 | 12-98 |
| Post-Treatment | 9.38 | 14.47 | 1.00 | 0-58 |
| Problems with more strenuous physical activities | | | | |
| Pre-Treatment | 75.29 | 17.50 | 74.50 | 41-98 |
| Post-Treatment | 20.21 | 15.93 | 15.50 | 0-50 |
| Problems doing your job | | | | |
| Pre-Treatment | 36.21 | 28.70 | 35.5 | 0-95 |
| Post-Treatment | 4.50 | 8.30 | 0.00 | 0-29 |
| Reduced energy and strength | | | | |
| Pre-Treatment | 69.29 | 15.08 | 66.5 | 37-98 |
| Post-Treatment | 13.25 | 15.25 | 8.00 | 0-50 |
| Low spirit | | | | |
| Pre-Treatment | 67.21 | 21.09 | 70.50 | 6-98 |
| Post-Treatment | 12.00 | 12.41 | 9.00 | 0-51 |
| Reduced social life | | | | |
| Pre-Treatment | 58.42 | 27.02 | 67.50 | 10-98 |
| Post-Treatment | 11.00 | 12.72 | 7.50 | 0-50 |
| Problems sleeping | | | | |
| Pre-Treatment | 66.13 | 23.75 | 73.00 | 18-97 |
| Post-Treatment | 11.04 | 11.46 | 9.50 | 0-50 |

Note.
M = Mean;
SD = Standard Deviation;
Mdn = Median.
Possible Range for each DoloTest item is 0-100.

Discussion

One of the most interesting aspects of the work of the current inventors is that HCG appears to be very effective in treating chronic pain and other sequelae of central sensitization at 120-170 IU/day, and more especially 140-160 IU/day, but not at other dosages. Thus, a dosages of 200 IU/day, 300 IU/day and 500 IU/day are all markedly less effective, and lower dosages are also markedly less effective. This seems to be true regardless of age (at least for adults), gender, weight, and other factors.

Although this specification and the appended claims should not be limited by the validity of any particular theory or mechanism of action, the current inventors have contemplated a theoretical framework that may have significant validity in explaining the surprising results discussed herein.

HCG is now recognized to have pleiotropic actions throughout the body as evidenced by the documented presence of receptors for HCG in multiple cellular compartments including the CNS. See Rao C V. An overview of the past, present, and future of non-gonadal LH/hCG actions in reproductive biology and medicine. Semin Reprod Med, 2001; 19:7-17; and Lei Z M, Rao C V. Neural actions of luteinizing hormone and human chorionic gonadotropin. Semin Reprod Med, 2001; 9:103-109. The exact functioning of these receptors is not fully elucidated but indications regarding their putative functions have been delineated as the current inventors will cite below.

In the adult CNS, HCG receptors have been established to be present in the hippocampal formation, hypothalamus, cerebral cortex, brain stem, cerebellum, pituitary gland, neural retina, spinal cord and the ependymal region (Lei Z M, Rao C V, Kornyei J L, Licht P, Hiatt E S. Novel expression of human chorionic gonadotropin/luteinizing hormone receptor gene in brain. Endocrinology, 1993;132:2262-2270). Both neurons and glial cells are shown to express receptors for HCG (Lei Z M, Rao C V, Kornyei J L, Licht P, Hiatt E S. Novel expression of human chorionic gonadotropin/luteinizing hormone receptor gene in brain. Endocrinology, 1993;132:2262-2270). Furthermore, it is postulated that HCG may play an important signaling role in differentiation and development of tissue subsets from germ cell layering during blastocyst stage (Gallego M J, Porayette P, Kaltcheva M M The Pregnancy Hormones HCG and Progesterone Induce Human Embryonic Stem Cell Proliferation and Diferentiation into Neuroectodermal Rosettes. Stem Cell Research and Therapy 2010; 1:28) to organ development during fetal life (Abdallah M A, Lei Z M, Li x, Greenwold N Human Fetal Non-Gonadal Tissues Contain HCG/LH Receptors. J Clin Endo Metabol 2004; 89:952-56) and perhaps on some more subtle, yet clinically significant way, in adults. Recent evidence confirms the presence of HCG receptors in the adult CNS, and additional evidence supports HCG as a signaling hormone for tissue differentiation and growth. See also Rao C V, Lei Z M The past, present and future of non-gonadal LH/hCG actions in reproductive biology and medicine. Mol Cell Endocrinol. 2007 Apr. 15; 269(1-2):2-8.

Various models point to neuroplasticity effects which HCG, in appropriate dosing, can provide as the facilitator of the clinic benefits the current inventors see in chronic pain patients. Relevant to pain control, and in regard to the weight loss phenomenon the current inventors witness concomitantly, is the work of Meng, Wennert and Chan (Meng X, Rennert O, Chan, W Human chorionic gonadotropin induces neuronal differentiation of PC12 cells through activation of stably expressed lutropin/choriogonadotropin receptor. Endocrinology 2007; 48(12)5765-5873) who conducted a study on neuronal differentiation on PC12 cell lines derived from rat pheochromocytoma. This investigative platform is a well established and accepted theoretical model for study of neuronal differentiation and signaling in humans (Greene L A, Tischler A S Establishment of a noradrenergic clonal line of rat adrenal pheochromocytoma cells which respond to nerve growth factor. Proced Nat Acad Sci 1976. 73:2424-2428).

They showed that stimulation of HCG receptors present on these cells results in neuroplasticity effects including neuritogenesis and neurite outgrowth—expansion of cell size and establishing new more complex and functional network connections. Neuroplasticity is a term that denotes the capacity of neurons to alter functionality and, in this case to form new, or re-establish old, connections. In the context of neuroplasticity, HCG has been shown to stimulate neuronal differentiation of PC 12 cells. In the adult brain, although the majority of neurons are post-mitotic, there are multi-potent neural stem/progenitor cells generating young neurons throughout life as noted above (Colcci-D'Amato L, Bonavita V, di Porzio U. The end of the central dogma of neurobiology: stem cells and neurogenesis in adult CNS. 2006 Neurol Sci. 27:266-270). Animal models in support of this idea demonstrate evidence of neuroplasticity and neuronal renewal stimulated by HCG. One group reported that HCG administration in animals with spinal cord injury can significantly improve recovery of motor function (see Patil A A, Nagaraj M P. The effect of human chorionic gonadotropin (HCG) on functional recovery of spinal cord sectioned rats. Acta Neurochir (Wien) 1983(69):205-218).

Of further interest in the Meng study was that HCG concentrations were maintained in the 200-1000 ng/ml window for these effects. Earlier studies have shown that the above HCG effects on primary neurons and glial cells were significant only with ambient concentrations of 100-250 ng/ml of HCG. We believe there is a critical window of HCG concentration required to manifest these neuroplasticity effects which may explain the observed clinical activities. Concentrations too high may blunt this effect. This is consistent with other models of HCG action where concentrations in a narrow window were necessary for effect (Maymo J L, Perez A P, Sanchez-Margalet V, Duenas J L. Up-regulation of placental leptin by human chorionic gonadotropin. Endocrinology 2009; 150(1):304-313). This is postulated to be secondary to transient loss of second messenger production (desensitization) and/or loss of cell surface receptors (down regulation) in response to higher doses of the ligand. In the original work of Simeons et al. for HCG weight loss it become apparent that weight loss was seen only with parenteral administration of 100-200 IU/day and dosing above this level blunted the weight loss effect of his protocol (see Simeons ATW Pounds and Inches 1953 Internet Page 24). For example and conversely, in men treated for hypogonadism with much higher doses of HCG (5000 IU up to 7000 IU/week) the current inventors do not see this pain control phenomenon.

It is entirely conceivable that different concentrations of a hormone have different intended and possible effects at different thresholds in the body.

In a unifying concept, HCG administration within a narrow window of 140-170 IU/day will initiate a 'neuroplasticity effect' encompassing shifts in electrical signaling, intracellular molecular signaling and gene transcription resulting in analgesia in those with chronic, central sensitization mediated pain. The analgesic effect of HCG in specifically addressing central sensitization has not previously been identified by the medical community.

Considering the rapidity of responses observed in our retrospective series, the current inventors postulate that the initial and perhaps sustained responses in patients would result from immediate neuroplasticity effects.

An example of this type of immediate neuroplasticity effect might include the following: In the suggested model for the 'central sensitization' theory of chronic pain, it has been documented that glial cells, in this setting, are a source of maladaptive secretion of inflammatory mediators (nitric oxide, reactive oxygen species, prostaglandins, pro-inflammatory cytokines, nerve growth factor) that serve to facilitate continued release of excitatory neurotransmitters such as Substance P and glutamate which serve to enhance post-synaptic hyperexcitability of pain transmission neurons (PTN) which augments transmission of pain signals resulting in the hyperalgesic and allodynic responses seen with central sensitization phenomenon and chronic pain. Our theory is that HCG might have a beneficial neuroplasticity effect on these glial cells and shift their function away from the release of these mediators to a more normal physiologically functional state associated with dampening or elimination of chronic pain. See also Bradley L A. Pathophysiology of fibromyalgia. Am J Med. 2009 December; 122(12 Suppl) S22.

This represents one example, or part, of what the current inventors theorize is a synergistic pattern of pleiotropic effects that HCG might exert on several levels within the CNS and Peripheral Nervous System (PNS) to restore order and thereby reduce pain. Neural damage to either the PNS or CNS provokes a maladaptive neuroplasticity response in nociceptive pathways that drive spontaneous pain and sensory amplification. This maladaptive plasticity leads to persistent changes which, as mentioned earlier, should be considered a true disease state. In the CNS; gene dysregulation, synaptic facilitation, loss of pain inhibition pathways at multiple levels in the neuraxis all work in concert leading to central amplification of pain signaling. Additionally, neurite death and altered synaptic connectivity serve as a foundation for chronic altered processing of both nociceptive and innocuous afferent inputs. See Costgan M, Scholz J, Woolf C J Neuropathic pain: A maladaptive response of the nervous system to damage Annu Rev Neurosci. 2009; 32:1-32.

Given the multitude of intertwined and interconnected genetic, cellular and molecular components that cause chronic neuropathic pain, targeted pharmacotherapy will most often lead to disappointing results as it is difficult to create a single agent that would modulate this multi-faceted pathophysiology to obtain the desired effect.

On a broader level, the current inventors view that, HCG administration in specific low dosing ranges has the ability to rejuvenate us in certain ways that re-establish normal physiology and function, whether that be a return to normal size in a weight loss program, or a return to 'normal' or m ore functional pain transmission pathways that result in decreased chronic pain. The current inventors postulate, from the above, that it is HCG that plays a principle role in re-setting physiological function at different levels. What better place to look for clinical answers when pathology develops as adults if the machinery—or the blueprint for functionality—is still in place and available? It would just require the appropriate activation, which the current inventors believe the current inventors may be observing with these reported cases. HCG carries the innate information, or signaling capacity, to allow for these cellular plasticity effects that can facilitate a return to 'normal' homeostasis or healthy cellular functioning and concomitant diminution or elimination of pain.

Whatever the mechanism may prove to be when elucidated exactly, the current inventors postulate that administration of HCG parenterally in dosing of 140-170 IU/day is a non-toxic intervention for pain control relative to the toxicity and QOL burdens associated with the pain control interventions our patients required prior to HCG treatment. Compliance with daily injections was 100%.

With regard to fibromyalgia, a complex, poorly understood disorder that has as a central component, chronic neuropathic pain, even the FDA approved medications to treat fibromyalgia pain—two of which are in fact antidepressants—have no effect on depression and anxiety also associated with this disorder. The current inventors have found that HCG, through its pleiotropic, synergistic neuroplasticity effects results in a marked improvement in depressive symptoms for those in our series. The DoloTest™ Spiritual/Social/Sleep construct findings clearly demonstrate this clinical effect and are supported by the information below. This is a remarkable additional benefit for these patients. See Recla J. New and emerging therapeutic agents for the treatment of fibromyalgia: an update J Pain Res. 2010; 3: 89-103.

It has been noted that Major Depressive Disorder (MDD) and any chronic pain syndrome often present as co-morbid conditions (30-60% of cases in one report) (Bair M J, Wu J, Damush T M, Sutherland J M, Kroenke K. Association of depression and anxiety alone and in combination with chronic musculoskeletal pain in primary care patients. Psychosom Med, 2008: 70(8);890-7).

The present results suggest that HCG acts similarly on neural pathways involved in MDD that are subject to a very similar sensitization or 'kindling' phenomenon (implies that each episode of depression make subsequent depressive episodes more likely and less dependent upon an external stimulus such as stress or sickness), where cellular structure and function are modulated and modified through many of the same CNS synaptic, cell signaling and transcriptional pathways, to effect depression. An excellent review on this very topic posits that there may indeed be a shared neurobiological basis of MDD, FM, neuropathic pain, and other chronic pain syndromes which makes the option of HCG treatment an even more intriguing concept as it may, as a single agent, truly address these related and co-morbid CNS disorders concomitantly and with minimal toxicity as compared with current available options (Maletic V., Raison CL Neurobiology of depression, fibromyalgia and neuropathic pain. Frontiers in Bioscience. Jun. 1, 2009; (14):5291-5338). Robert Post first proposed that 'kindling' and sensitization may have similar neurobiological underpinnings, such as neuroplastic changes and alterations in gene expression (Post RM. Kindling and sensitization as models for affective episode recurrence, cyclicity, and tolerance phenomena).

Others have reported on the use of HCG for purported pain control but have advocated for higher dosing, far above what the current inventors have used and are recommending. Tennant recommends in this report using 500 to 1000 IU given 1-3 times per week and reports pain control. However, the one quantified case referenced still required 1400 mg of morphine for pain control from a baseline of 3500 mg (Tennant F. Human chorionic gonadotropin: Emerging use in pain management. 2010 Published on Internet and in Practical Pain Management, Jun. 1, 2009). Also, these higher doses advocated would run a significant risk of ovarian hyper-stimulation in women who still have their ovaries, it should be noted. One could also surmise that if larger dosing such as this were to have a significant analgesic effect, this would have been observed on a larger scale in the many thousands of patients treated long term for male hypogonadism on similar dosing regimens. To our knowledge, there are no such reports.

We believe that HCG, used in the fashion described here, will prove to be a useful clinical adjunct in the treatment of any chronic pain condition where central sensitization pathways are at work. Whether this is due to an initial peripheral insult that has been perpetuated through damage or injury to PNS or CNS structures, or in those cases where the initial insult is unknown or unclear, but central sensitization pathways have nonetheless been activated. These disorders would include fibromyalgia; osteoarthritis; rheumatoid arthritis; neuropathy and chronic pain resulting from bulging vertebral discs; chronic pain resulting from CNS insults such as stroke, spinal cord injury and multiple sclerosis; and PNS lesions or diseases including: direct nerve trauma, toxic and metabolic neuropathies, herpes zoster and AIDS.

Along with a significant decrease in the pain index and a significant improvement in the other DoloTest™ items score, our results demonstrate that there is a significant interdependence of the DoloTest™ items with the amount of pain experienced by the patients, which points to a major contribution of the former to the sense of physical and spiritual well-being perceived by the patients. As such, an effect of treatment on mood, energy, and self-perception of the patients may have become manifest.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context.

Where the specification claims refers to at least one of something selected from the group consisting of A, B, C . . . and N, the text should be interpreted as requiring only one element from the group, not A plus N, or B plus N, etc. Additionally, although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

What is claimed is:

1. A method of treating a central sensitization disorder selected from the group consisting of fibromyalgia, irritable bowel syndrome, a chronic arthropathy, post herpetic neuralgia, trigeminal neuralgia, an autonomic neuropathy, a metabolic neuropathy, a post-surgical pain syndrome, a spinal nerve compression syndrome, a migraine, and osteoarthritis in a subject in need thereof comprising:
administering to the subject subcutaneously a daily dosage of human chorionic gonadotropin (HCG) of between 120 IU/day and 170 IU/day, inclusive, wherein at least one symptom associated with the central sensitization disorder is ameliorated following administration.

2. The method of claim 1, wherein the subcutaneous dose is between 140 IU/day and 160 IU/day, inclusive.

3. The method of claim 2, wherein the subcutaneous dose is 150 IU/day.

4. A method of treating chronic pain associated with a central sensitization disorder selected from the group consisting of fibromyalgia, irritable bowel syndrome, chronic arthropathy, post herpetic neuralgia, trigeminal neuralgia, an autonomic neuropathy, a metabolic neuropathy, a post-surgical pain syndrome, a spinal nerve compression syndrome, migraine, and osteoarthritis in a subject in need thereof comprising:
administering to the subject subcutaneously a daily dosage of HCG of between 120 IU/day and 170 IU/day, inclusive, wherein the chronic pain is ameliorated following administration.

5. The method of claim 1, wherein the HCG is administered via an auto-inject pen or dial-up dosing pen.

6. The method of claim 1, wherein the HCG is purified from the urine of pregnant women.

7. The method of claim 1, wherein the HCG is recombinant HCG.

8. The method of claim 1, wherein the subject is not receiving concomitant treatment with an opioid.

9. The method of claim 1, wherein the subject is not receiving concomitant treatment with another gonadotropin.

10. The method of claim 1 or 4, wherein the central sensitization disorder is fibromyalgia.

11. The method of claim 4, wherein the daily dosage of HCG is at a subcutaneous dose between 140 IU day and 160 IU day, inclusive.

12. The method of claim 4, wherein the daily dosage of HCG is at a subcutaneous dose of 150 IU.

13. The method of claim 4, wherein the chronic pain associated with a central sensitization disorder is chronic pain associated with a post-surgical pain syndrome or a spinal nerve compression syndrome, and results from bulging or herniated vertebral discs, spinal cord injury, neoplasia, or surgery.

14. The method of claim 4, wherein the chronic pain is ameliorated within one to two days following commencement of the method.

15. The method of claim 4, wherein the subcutaneous daily dose of HCG is administered via an auto-inject pen or dial-up dosing pen.

16. The method of claim 4, wherein the HCG is purified from the urine of pregnant women.

17. The method of claim 4, wherein the HCG is recombinant HCG.

18. The method of claim 4, wherein the subject is not receiving concomitant treatment with an opioid.

19. The method of claim 4, wherein the subject is not receiving concomitant treatment with another gonadotropin.

20. The method of claim 1 or 4, wherein the HCG is administered on a daily basis without signs of toxicity.

21. The method of claim 1 or 4, wherein the central sensitization disorder is osteoarthritis.

22. The method of claim 1 or 4, wherein the central sensitization disorder is a chronic arthropathy.

23. The method of claim 22, wherein the chronic arthropathy is selected from rheumatoid arthritis, arthritic arthropathy, and psoriatic arthritis.

24. The method of claim 1 or 4, wherein the central sensitization disorder is a migraine.

25. The method of claim 1 or 4, wherein the central sensitization disorder is a post-surgical pain syndrome.

26. The method of claim 25, wherein the post-surgical pain syndrome is a result of a surgery selected from a thoracotomy, a mastectomy, and an amputation.

27. The method of claim 26, wherein the HCG is administered perioperatively.

28. The method of claim 5 or 15, wherein the auto-inject pen or dial-up dosing penis pre-set to administer the daily dosage of HCG.

* * * * *

UNITED STATES PATENT AND TRADEMARK OFFICE
CERTIFICATE OF CORRECTION

PATENT NO. : 8,680,086 B2  Page 1 of 1
APPLICATION NO. : 13/211101
DATED : March 25, 2014
INVENTOR(S) : Edson Conrad Hicks, Jr. and Constance T. Dutton It is certified that error appears in the above-identified patent and that said Letters Patent is hereby corrected as shown below:

In the Claims:

Column 17, Line 33 (Claim 11), please delete "IU day" and insert -- IU/day --, therefor.

Column 17, Line 34 (Claim 11), please delete "IU day," and insert -- IU/day, --, therefor.

Column 17, Line 36 (Claim 12), please delete "IU." and insert -- IU/day. --, therefor.

Column 18, Line 37 (Claim 28), please delete "penis" and insert -- pen is --, therefor.

Signed and Sealed this
First Day of July, 2014

Michelle K. Lee
*Deputy Director of the United States Patent and Trademark Office*